(12) United States Patent
Armini

(10) Patent No.: US 6,264,598 B1
(45) Date of Patent: Jul. 24, 2001

(54) PALLADIUM COATED IMPLANT

(75) Inventor: Anthony J. Armini, Manchester-by-the-Sea, MA (US)

(73) Assignee: Implant Sciences Corporation, Wakefield, MA (US)

(*) Notice: Subject to any disclaimer, the term of this patent is extended or adjusted under 35 U.S.C. 154(b) by 0 days.

(21) Appl. No.: 09/366,022

(22) Filed: Aug. 2, 1999

Related U.S. Application Data

(60) Provisional application No. 60/095,558, filed on Aug. 6, 1998.

(51) Int. Cl.[7] ..................................................... A61N 5/00
(52) U.S. Cl. ............................................ 600/3; 600/8
(58) Field of Search ...................... 600/1–8; 424/1.29

(56) References Cited

U.S. PATENT DOCUMENTS 5,395,300 * 3/1995 Liprie ........................................ 600/3
5,405,309 * 4/1995 Carden, Jr. ................................ 600/8
6,143,431 * 11/2000 Webster .................................... 600/8

* cited by examiner

*Primary Examiner*—John P. Lacyk
(74) *Attorney, Agent, or Firm*—Foley, Hoag & Eliot, LLP

(57) ABSTRACT

The present invention provides methods and devices which use a palladium source enriched in Pd-102 and depleted in Pd-108 and Pd-110 to coat the body of a medical device. Whereas prior devices, which include palladium throughout the volume of the body, require the use of highly enriched palladium sources to counteract the effect of absorption of radiation by palladium and other metals in the body, devices wherein palladium is located primarily on the surface of the body more efficiently deliver therapeutic radiation to the target tissue, and thus can employ less highly enriched palladium sources. Such palladium sources are significantly less expensive than highly enriched sources, thereby greatly reducing the cost of devices and methods which use such a coating of palladium.

13 Claims, 2 Drawing Sheets

PALLADIUM COATED IMPLANT

RELATED APPLICATIONS

This application is based on and claims priority to provisional application Ser. No. 60/095,558, filed Aug. 6, 1998, which is hereby incorporated herein by reference.

BACKGROUND OF THE INVENTION

Radioactive seeds are routinely implanted to treat cancers, such as prostate cancer. The radioactive elements iodine-125, which has a 60-day half-life and emits a 31 keV x-ray, and palladium-103, which has a 17-day half-life and emits a 21 keV x-ray, both emit only soft x-rays from electron capture decay and are widely used in seeds for this type of radiotherapy.

Co-pending U.S. patent application Ser. No. 09/047,728 teaches a method of ion-implanting the precursor isotope Xe-124 into an aluminum pellet and subsequently activating the Xe-124 in a nuclear reactor to produce I-125 embedded beneath the surface of the aluminum pellet. Using this method for a palladium seed, however, would be extremely expensive because palladium which has been extensively enriched for Pd-102, which is the preferred activatable isotope, is costly. For example, 78% enriched Pd-102 (e.g., having 78% Pd-102) is available from Oak Ridge National Laboratory at a cost of approximately $867,000 per gram. Pd-104 and Pd-105 provide the balance of the palladium in this material, and it is substantially free of Pd-106, Pd-108, and Pd-110. The presence of Pd-108 and Pd-110 in particular is undesirable because, upon activation, these isotopes tend to form long-lived gamma-emitting isotopes.

U.S. Pat. No. 4,702,228 to Russell teaches using a substantially enriched separated isotope (i.e., enriched to a minimum of 50% Pd-102) to fabricate radioactive interstitial implants emitting radiation from Pd-103. The disadvantage of using this highly enriched, separated Pd-102 is that it is extremely expensive and is difficult to obtain in sufficient quantities. Russell teaches that this highly enriched isotope is necessary because natural palladium contains only about 1% Pd-102 and the remainder of the palladium absorbs much of the x-ray intensity generated by the radioactive Pd-103. However, the Russell design uses two spherical pellets approximately 0.6 mm in diameter in which the enriched palladium is distributed uniformly throughout the volume of the pellet. This design contributes to self-absorption because radiation from palladium atoms located away from the surface of the pellets must travel to the surface of the pellet without being absorbed along the way.

SUMMARY OF THE INVENTION

The present invention comprises an implantable article having disposed on all or a portion of the surface thereof a coating or layer of palladium which either contains a therapeutic amount of radioactive Pd-103, or contains an amount of non-radioactive precursor isotope Pd-102 sufficient to provide a therapeutic amount of Pd-103 upon thermal neutron activation. Because the palladium-coated article of the present invention has the palladium layer disposed on the exterior surface of the article rather than distributed throughout its volume, the distance radiation emitted from Pd-103 must travel to reach the surface is minimized. Thus, Pd-103 emissions are utilized more efficiently, and the palladium used in the coating or layer may contain a lower concentration of Pd-102 than is necessary in designs wherein the palladium is distributed throughout the volume of a device.

In one aspect, the invention comprises medical devices comprising a body having disposed thereon a coating or layer of palladium which is moderately enriched in Pd-102 and preferably substantially depleted in Pd-108 and Pd-110. The device may additionally comprise a coating, shell or container of a biocompatible material disposed on or surrounding the palladium-coated device. In certain embodiments, an adhesion layer may be deposited between the palladium layer and the body, or between the palladium and the biocompatible coating.

The device comprises a layer of palladium enriched in Pd-102 disposed on all or a portion of an exterior surface of the body. Pd-102 is a non-radioactive precursor isotope which can be activated in a nuclear reactor to form the radioactive isotope Pd-103. In preferred embodiments, the palladium layer is substantially depleted in Pd-110 and Pd-108. Upon exposure to thermal neutrons, some or all of the Pd-102 in the palladium layer may be converted to Pd-103. The amount of palladium disposed on the body is preferably sufficient to provide, upon activation of Pd-102 to Pd-103, a therapeutic dose of radiation. Preferably, the palladium layer is enriched to contain up to about 10% Pd-102, and more preferably, from about 2% to about 8% Pd. A layer of Pd having a thickness of from about 2 microns to about 10 microns is sufficient for this purpose. In a currently preferred embodiment, the palladium layer is from our 3 microns to about 8 microns thick.

In another aspect, the invention comprises an implantable radioactive device wherein the palladium layer includes Pd-103. In such embodiments, the palladium layer disposed on the body is enriched in Pd-102 and Pd-103, for example, up to about 10% Pd-102 and Pd-103 together, and preferably is substantially depleted in Pd-110 and Pd-108. In certain embodiments, the palladium layer comprises an amount of Pd-103 sufficient to provide a therapeutic dose of radiation. In a currently preferred embodiment, the radioactive device has an activity of between about 0.1 and about 10 millicuries. A layer of Pd having a thickness of from about 2 microns to about 10 microns is sufficient for this purpose.

A body useful in the medical device of the present invention comprises any structure, device or article having characteristics such as stability, resiliency, structure, and shape suitable for use as an implantable radioactive medical device. The body may comprise, for example, a stent, seeds, a wire, a wire segment, or other article suitable for implantation in a patient to deliver a localized dose of radiation. In a currently preferred embodiment, the body comprises a wire segment. The body may comprise any material suitable for use in an implantable medical device. The body material preferably comprises a metal, metal alloy, or ceramic. For example, a titanium alloy, titanium-vanadium-aluminum alloy, rhodium, vanadium, aluminum or combinations of these materials may be used. Ceramics useful in the present invention may comprise, for example, quartz (silicon dioxide), alumina (aluminum oxide) and titania (titanium dioxide).

The device may additionally include an adhesion layer disposed between the palladium layer and the body. The adhesion layer comprises a material, preferably a metal, which improves adhesion of the palladium to the body. The adhesion layer preferably comprises at least one material selected from the group consisting of aluminum, silicon, titanium, vanadium, and rhodium. The currently preferred material is titanium. The adhesion layer may be of any thickness sufficient to improve the adhesion of the palladium layer to the body, and preferably is as thin as possible to avoid altering the physical properties of the device. For example, the adhesion layer preferably is less than about 2000 Å thick, more preferably less than about 500 Å thick.

The device may further comprise a coating, layer, shell or capsule of biocompatible material disposed on and substantially surrounding (e.g., encapsulating) the palladium layer. Suitable biocompatible materials include titanium, stainless steel and combinations thereof. The biocompatible coating may be of any thickness that provides the desired encapsulation. A biocompatible coating used for encapsulation preferably is as thin as possible so as not to impede radiation emitted from Pd-103. For example, the biocompatible coating preferably is less than about 50,000 Å thick, more preferably less than about 10,000 Å thick, depending on the composition of the materials used and the radiation dosage desired for the targeted tissue. Alternatively, the biocompatible shell or sealed capsule of titanium between about 0.0025 and about 0.0125 cm thick. An adhesion coating, such as described above, may be included between the palladium layer and the biocompatible layer.

In one embodiment, the device may comprise a canister having disposed therein at least one device coated with enriched Pd-102 or activated Pd-103 as described herein. The canister preferably is formed of a biocompatible material, such as those described above. Optionally, a radiopaque pellet or wire may be disposed within the canister.

The invention also comprises methods for making radioactive medical devices. In one aspect, the method comprises contacting a body with palladium enriched in Pd-102 under conditions sufficient to cause the palladium to become disposed on, associated with, or carried with the body. The palladium layer optionally may contain other precursor isotopes which can be activated to form radiotherapeutic radioactive isotopes, for example, Xe-124, which can be activated to form I-125. The body and the stable precursor element(s) may then be exposed to a source of thermal neutrons, e.g., in a nuclear reactor, under conditions sufficient to form the desired radioactive isotopes. A biocompatible coating may be disposed on the device before or after thermal neutron activation. Furthermore, an adhesion coating may be disposed on the body before contacting the body with palladium. Similarly, an adhesion coating may be disposed on the palladium layer prior to coating the body with a biocompatible material. In certain embodiments, two or more of the above layers may be applied substantially simultaneously.

The palladium layer may be disposed on the body by coating the elements onto the surface of the body, sputtering the elements onto the surface of the body, applying the elements to the body by physical vapor deposition, electroplating the elements onto the surface of the body, or some combination thereof. As described above, the palladium used in this layer preferably is enriched in Pd-102, for example, up to about 10%, and preferably is substantially depleted in Pd-110 and Pd-108.

The Pd-102 is activated by exposing the device to a source of thermal neutrons under conditions sufficient to generate Pd-103, preferably in an amount capable of delivering a therapeutic dose of radiation. The body and any layers disposed thereon during activation preferably do not include materials, such as stainless steel, chromium, or nickel, which may generate undesirable radioisotopes when exposed to a source of thermal neutrons, unless the duration of the exposure is limited. In one embodiment, the body is substantially free of isotopes which significantly thermal neutron activate to radioisotopes having half lives between about 16 hours and about one million years. Exposing the device to a source of thermal neutrons may comprise thermal neutron-activating the Pd-102 at a dosage between approximately $1 \times 10^{17}$ neutrons/cm$^2$ and $1 \times 10^{20}$ neutrons/cm$^2$, or between any of the subranges and variations of such dosage.

The methods of the present invention may further comprise applying a biocompatible coating, as described above. The biocompatible coating may be applied to at least a portion of the body by any coating method, for example by sputtering, physical vapor deposition, electroplating, or some combination thereof. In certain embodiments, an adhesion coating is applied prior to applying the biocompatible coating. In certain other embodiments, the biocompatible coating may be applied substantially simultaneously with the enriched Pd-102 layer, e.g., by sputtering the two materials substantially simultaneously.

There will generally be some absorption of the radiation by the biocompatible material, and such absorption will tend to diminish the amount of radiation delivered to the tissue to be treated. Thus, the desired radiation dosage amount and the attenuation factor may be considered in determining the quantity of Pd-102 to be used and the duration of the thermal neutron activation period.

An adhesion layer, as described above, may be deposited onto the body before coating with palladium, or before deposition of the biocompatible coating. The adhesion layer may be deposited by any of a variety of well known coating methods, such as thermal boat evaporation, electron beam evaporation, sputtering, electroplating, or some combination thereof.

In one embodiment, the method further may comprise placing the at least one body into a canister, such as a titanium canister, and sealing the canister by any means known in the art, e.g., by welding one or more end-caps, such as titanium end-caps, on the canister to form a sealed container. Optionally the method may further comprise placing at least one pellet of a radiopaque material into the canister.

The invention further comprises a method of treatment of a cancerous tumor by exposing the tumor to a radioactive implant made according to the present invention. For example, a radioactive implant prepared as described above may be placed in an area of tissue affected by the tumor, thereby permitting a therapeutic dosage of radiation to be delivered to the cancerous tumor.

DETAILED DESCRIPTION OF THE INVENTION

The present invention relates to comprising a body having disposed on all or a portion of a surface thereof a layer of palladium enriched in Pd-102, e.g., up to about 10%. The palladium-coated device then is activated to convert at least a portion of the Pd-102 to the radioactive isotope Pd-103. This disposition of the palladium increases the efficiency of radiation from activated Pd-103, thereby allowing the use of palladium less enriched in Pd-102 than is necessary for devices wherein the palladium is disposed throughout the body. The palladium preferably is substantially depleted of Pd-110, and preferably depleted of most Pd-108, because these isotopes can thermal neutron activate to isotopes which generate undesirable high energy gamma rays. Typically, these isotopes may be substantially depleted by moderate enrichment of Pd-102, e.g., to up to about 10%.

In an exemplary embodiment, palladium enriched in Pd-102 is provided as a thin layer on a device, such as a cylindrical wire or a pellet, rather than being distributed through the volume of the device. An enrichment of Pd-102 to about 10% or less is adequate to achieve the desired depletion of Pd-108 and Pd-110, thus minimizing undesired gamma rays that may result from activation of these isotopes. Preferably, the palladium is enriched in Pd-102 to a concentration of from about 3% to about 8%.

The thickness of the palladium coating or layer preferably is about 10 microns or less, more preferably from about 3 microns to about 8 microns thick. For a surface area of approximately 0.1 cm$^2$, a palladium coating of about 3–8 microns in thickness achieves the required radioactivity after activation. At this thickness, the self-absorption of the x-rays within the coating is minimal, e.g., only about 2% absorbed per micron of coating thickness.

Figure 1:
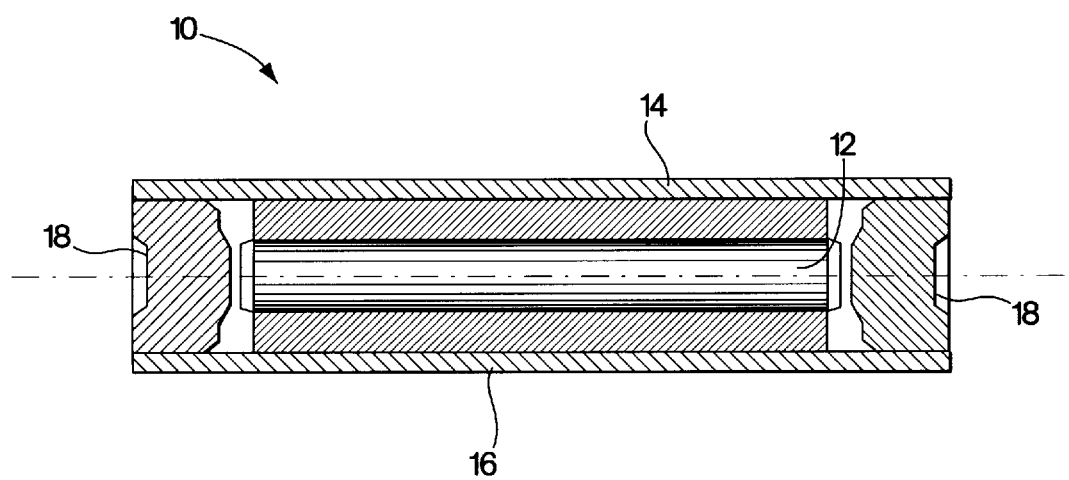
FIG. 1 is a schematic illustration of a side view of a radioactive device according to the invention.

FIG. 1 shows a currently preferred embodiment of a medical device 10 according to the present invention. A length of aluminum clad copper wire 12 has disposed thereon a layer of Pd-102 enriched palladium 14. End caps 18 are disposed at both ends to seal the shell thereby encapsulating the coated wire.

Figure 2:
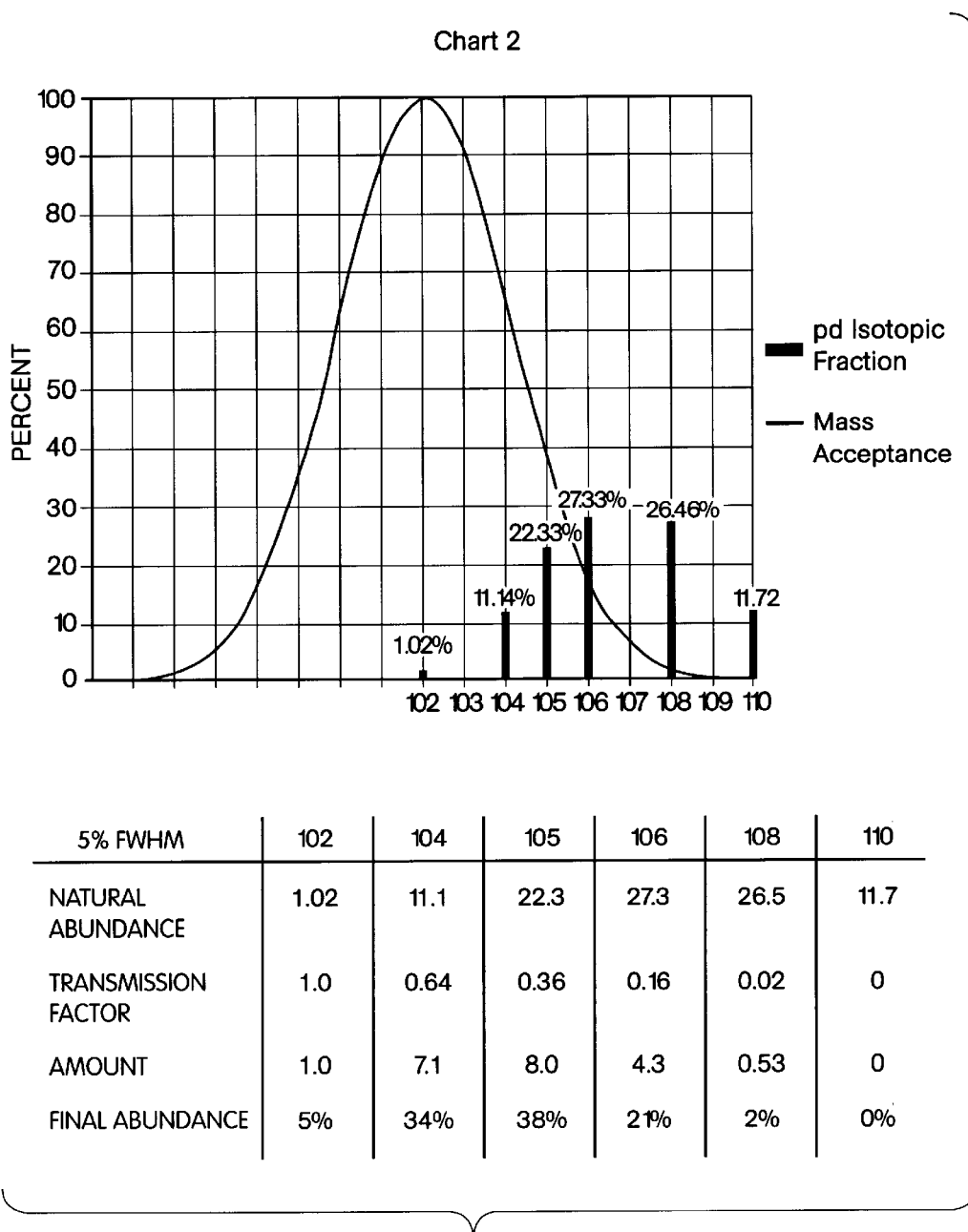
FIG. 2 is a graph showing the method of enriching palladium to 6% Pd-102 using a calutron with 5% full-width at half maximum acceptance resolution.

Palladium substantially depleted of Pd-110 and Pd-108 and slightly enriched in Pd-102 can be obtained commercially or can be generated using known technology. For example, Pd-102 enriched palladium can be prepared in sufficient quantities using a conventional calutron, as is well known in the art. Construction and operation of a low-resolution calutron capable of producing larger quantities than the high-resolution calutrons used to produce more highly enriched palladium, such as the 78% enriched palladium described above. For example, an ion implantation machine can be modified to separate palladium isotopes by this method. FIG. 2 is a graph showing how, using a low-resolution calutron, the abundances of each of the palladium isotopes can be altered to produce enrichment of Pd-102, eg., to about 5%, and a substantial depletion of Pd-108 and Pd-110, eg., to less than about 2% and 0.01%, respectively. This procedure simultaneously depletes the palladium of undesirable Pd-110 and Pd-108, and enriches the amount of Pd-102 to provide a palladium source suitable for use in the devices and methods described herein.

Preparation of a radioactive device can be achieved exposing a palladium-coated device of the present invention to thermal neutron activation under conditions sufficient to convert Pd-102 to Pd-103. The amount of exposure required for neutron activation of the medical device depends on, for example, the flux rate of the nuclear reactor used, the thickness and composition of the coating applied to the body, and the amount of radiation desired. The exposure time could range from several days in a very high flux reactor to a month in a low flux reactor.

When the Pd-103 is exposed to neutron activation in a nuclear reactor, other materials in the body of the medical device may also be activated. If the medical device body contains significant quantities of nickel, undesirable long-lived emissions of nickel-63 typically are produced. This isotope decays solely by beta decay with no gamma radiation. The beta end-point energy is 66.9 keV. The beta particles emitted by nickel-63 would continuously bombard the patient for the lifetime of the patient, because the half life of nickel-63 is 100 years. If the medical device body contains a significant quantity of nickel, a coating of a high-density, biocompatible material may be applied over at least a portion of the body. This coating may serve several useful purposes, including containment of undesirable beta particles from long-lived radioactive species or creation of a biologically inert surface.

Optionally, one or more adhesion layers may be disposed on the body to promote adhesion of the biocompatible coating material, and/or the enriched palladium. The adhesion layer may be formed a material that includes silicon, aluminum, titanium, vanadium, praseodymium, or rhodium when used between the body and the Pd-102. When deposited onto a previously radioactivated body, the adhesion layer preferably comprises silicon, titanium, vanadium or chromium when used between the radioactive body of the medical device and the biocompatible coating material. When deposited onto a body of a medical device prior to neutron activation, the adhesion layer preferably comprises silicon, titanium or vanadium. Materials containing substantial amounts of iron and chromium preferably should not be deposited as part of the adhesion layer or the high-density layer prior to neutron activation because such materials can produce undesirable long-lived radioisotopes that emit gamma rays.

The selection of biocompatible coating materials and adhesion layer materials is dependent on whether these materials will be subjected to neutron activation. If materials in either the biocompatible coating or the adhesion layer of a device which will undergo thermal neutron activation can also be neutron-activated to radioactive isotopes, it is preferable that the half-lives of any such radioactive isotopes be shorter than one day, so that these isotopes can be expected to decay to insignificant activity levels before the device is implanted. The elements aluminum, silicon, titanium, vanadium, manganese, copper, praseodymium, and rhodium meet this criterion.

In a currently preferred embodiment, a device according to the present invention comprises a wire segment for a body. The wire segment may be fabricated from hyperpure copper or aluminum clad copper, or any other suitable material as set forth above. Enriched palladium, as discussed above, is disposed, preferably by electroplating, on some or all of the surfaces of the wire segment, for example, to a thickness of about 3 microns. A 3 micron thick coating of 5% enriched palladium includes about 15 micrograms of Pd-102. The wire may then be thermal neutron activated to produce a radioactive source. The radioactive source then can be encapsulated in a shell of a biocompatible metal to produce a sealed device. An exemplary procedure for producing such a device is described in detail in the example below. The following example is provided to further illustrate one embodiment of the present invention, and is not intended to be limiting in any way.

EXAMPLE 1

Aluminum clad copper wire segments 0.026" in diameter, 0.157" long were electroplated with a coating of palladium enriched to 5% Pd-102 and substantially depleted of Pd-108 and Pd-110. The segments were placed in the flux trap of the University of Missouri nuclear reactor for activation. The parameters of the experiment are listed below:

| | |
|---|---|
| Depleted Pd thickness | 3 microns |
| Pd-102 content | 15 microgram |
| Reactor Flux | $4.5 \times 10^{14}$ n⁰/cm²-sec |
| Activation time | 18 days |
| Cool time | 7 days |
| Total activity after cool | 1.5 millicurie |
| Apparent Pd-103 Activity | 1.0 millicurie |

After cooling for 7 days, the 12-hour activity from the copper and the few minute half-lives from the aluminum were totally decayed, and the total Pd-103 activity was 1.5 mC and the apparent activity (due to absorption by the wire itself) was 1.0 mC, which is the therapeutic activity per seed currently used for treating prostate cancer.

Equivalents

While the invention has been disclosed in connection with the preferred embodiments shown and described in detail, various equivalents, modifications, and improvements will be apparent to one of ordinary skill in the art from the above description. Such equivalents, modifications, and improvements are intended to be encompassed by the following claims.

What is claimed is:

1. An activatable medical device, comprising a body, and a layer of non-radioactive palladium disposed on said body, said layer being enriched in Pd-102 relative to naturally occurring palladium, substantially free of Pd-110, and comprising less than about ten percent Pd-102.

2. The device of claim 1, wherein the body is substantially free of isotopes which significantly thermal neutron activate to radioisotopes having half-lives between about 16 hours and about one million years.

3. The device of claim 1, further comprising a biocompatible coating disposed on the layer of palladium.

4. The device of claim 3, wherein said biocompatible coating comprises titanium.

5. The device of claim 4, wherein the biocompatible coating has a thickness of from about 0.0025 cm to about 0.0125 cm.

6. The device of claim 1, wherein the layer of palladium is less than about 10 microns thick.

7. A method for making a medical device, comprising providing a body, and disposing on the body a layer of non-radioactive palladium, said layer being enriched in Pd-102 relative to naturally occurring palladium, substantially free of Pd-110 and comprising less than about ten percent Pd-102.

8. The method of claim 7, further comprising exposing the body and the layer of palladium to a source of thermal neutrons, thereby activating said palladium.

9. The method of claim 7, wherein the body is substantially free of isotopes which thermal neutron activate to form radioisotopes having half-lives between about 16 hours and about one million years.

10. The method of claim 7, further comprising a biocompatible coating disposed on the layer of palladium.

11. The method of claim 10, wherein said biocompatible coating comprises titanium.

12. The method of claim 11, wherein the biocompatible coating has a thickness of from about 0.0025 cm to about 0.0125 cm.

13. The device of claim 7, wherein the layer of palladium is less than about 10 microns thick.

* * * * *